United States Patent

Tsubouchi et al.

[11] Patent Number: 4,525,290
[45] Date of Patent: Jun. 25, 1985

[54] PROCESS FOR IMPROVING TRACTION COEFFICIENT OF TRACTION DRIVE FLUID AT HIGH TEMPERATURES

[75] Inventors: Toshiyuki Tsubouchi, Kisarazu; Hitoshi Hata, Ichihara, both of Japan

[73] Assignee: Idemitsu Kosan Company Limited, Tokyo, Japan

[21] Appl. No.: 626,311

[22] Filed: Jun. 29, 1984

Related U.S. Application Data

[63] Continuation-in-part of Ser. No. 502,966, Jun. 10, 1983, abandoned.

[30] Foreign Application Priority Data

Jun. 24, 1982 [JP] Japan ................................ 57-107539
Feb. 21, 1983 [JP] Japan ................................ 58-26325

[51] Int. Cl.³ ............................................ C07C 13/50
[52] U.S. Cl. ........................................ 252/73; 252/9; 585/20; 585/21; 585/360
[58] Field of Search ................. 252/9, 73; 585/20, 21, 585/360

[56] References Cited

U.S. PATENT DOCUMENTS 3,411,369 11/1968 Hammann et al. ............. 252/52 R
3,440,894 4/1969 Hammann et al. ............. 252/52 R
3,925,217 12/1975 Green et al. .................... 252/52 R

FOREIGN PATENT DOCUMENTS 2081301 2/1982 United Kingdom .

Primary Examiner—A. Lionel Clingman
Assistant Examiner—Robert A. Wax
Attorney, Agent, or Firm—Walter H. Schneider

[57] ABSTRACT

A process for improving traction coefficient of traction drive fluid at high temperatures by using a compound represented by the general formulae (I), (II) or (III) as a base stock of traction drive fluid,

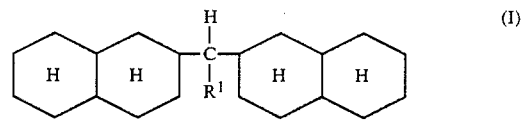

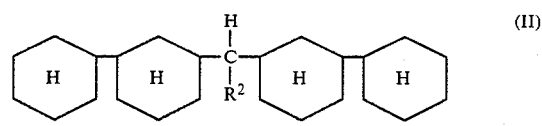

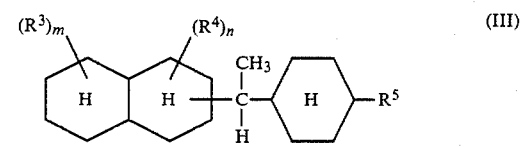

(All the symbols are as defined in the appended claims).

This process is helpful for reducing the change of traction coefficients over a wide range of from low temperature to high temperature.

24 Claims, 3 Drawing Figures

PROCESS FOR IMPROVING TRACTION COEFFICIENT OF TRACTION DRIVE FLUID AT HIGH TEMPERATURES

CROSS REFERENCE TO OTHER APPLICATION

This application is a continuation-in-part of application Ser. No. 502,966, filed June 10, 1983, now abandoned.

BACKGROUND OF THE INVENTION

The present invention relates to a process for improving traction coefficient of traction drive fluid at high temperatures. More particularly, it is concerned with a process for remarkably improving traction coefficient over a wide range of temperatures, especially at high temperatures by using specific compounds as a base stock of traction drive fluid.

A traction drive fluid is a fluid to be used in a traction drive (a friction driving device utilizing rolling contact), such as an automobile continuously variable transmission, an industrial continuously variable transmission, and a hydraulic machine, and needs to have a high traction coefficient and to be stable against heat and oxidation and be inexpensive.

In recent years, there has been the increasing trend toward miniaturization of a traction driving device using such a traction drive fluid and the use of such a device under high-speed, high-load conditions. Thus, it has been desired to develop a traction drive fluid of much higher performance.

In designing a traction driving device, it is generally said that the size of the traction driving device is in inverse proportion to the 0.45 power of a traction coefficient of a lubricant, provided that the traction driving device has the same service life and output ratio. Therefore, as the traction coefficient of a lubricant is higher, the traction driving device can be more reduced in size and weight. In this designing process, there is employed the minimum traction coefficient value in the temperature range within which the driving device is used; i.e., a traction coefficient value at the highest temperature within the foregoing temperature range because as the temperature increases, the traction coefficient value lowers. Therefore, a traction drive fluid having a high traction coefficient even at high temperatures is desirable for the miniaturization and weight-reduction of the traction driving device.

Also from a viewpoint of the use under high-speed, high-load conditions, it has been desired to develop a traction drive fluid having a high traction coefficient even at high temperatures.

Various types of compounds have been proposed as traction device fluids. Examples are described in, e.g., Japanese Patent Publication Nos. 338/1971, 339/1971, 35763/1972, 42067/1973, 42068/1973, and 36105/1978, and Japanese Patent Laid-Open Nos. 43108/1980, and 40726/1980. Although these compounds all have a high traction coefficient at low temperatures (from room temperature to 80° C. (176° F.)), they have disadvantages in that at high temperatures (from 80° to 140° C. (176°~248° F.)) the traction coefficient drops, or although the traction coefficient does not drop, the viscosity is high, resulting in a serious stirring loss. This will lead to a reduction in power transmission efficiency.

Further, U.S. Pat. No. 3,411,396 discloses traction drive fluids comprising fused saturated hydrocarbons. Though the fluids have a high traction coefficient over a temperature range of from room temperature to 200° F., the traction coefficient of the fluids drops seriously at temperatures of more than 250° F. Therefore, these traction drive fluids cannot be used for continuously variable transmission for cars which is driven at high temperatures.

U.S. Pat. No. 3,440,894 discloses a compound having cyclic group as traction drive fluids, and U.S. Pat. No. 3,975,278 discloses hydride of α-methylstyrene dimer as traction drive fluids. These compounds, however, have disadvantages in that the traction coefficient is lowered at high temperatures.

SUMMARY OF THE INVENTION

An object of the invention is to provide a process for improving traction coefficient at high temperatures.

Another object of the invention is to provide a process for reducing the change of traction coefficients over a wide range of from low temperature to high temperature.

Still another object of the invention is to provide a process for maintaining high traction coefficient even under severe conditions of high-speed and high-load.

The present invention relates to a process for improving traction coefficient of traction drive fluid at high temperatures by using a compound represented by the general formulae (I), (II), and (III) as a base stock of traction drive fluid;

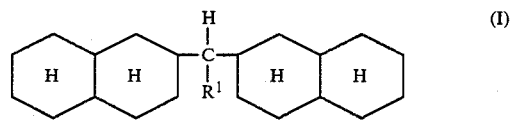

(I)

wherein $R^1$ is an alkyl group containing from 1 to 3 carbon atoms,

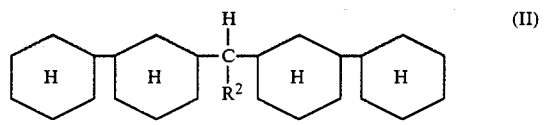

(II)

wherein $R^2$ is an alkyl group containing 1 or 2 carbon atoms,

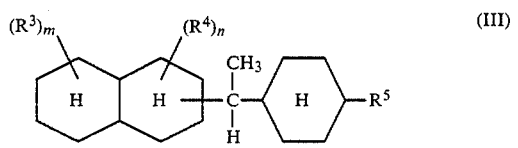

(III)

wherein $R^3$ and $R^4$ are each a hydrogen or a methyl group, $R^5$ is a hydrogen or a tert-butyl group, and m and n are each 1 or 2.

DETAILED DESCRIPTION OF THE INVENTION

Figure 1:
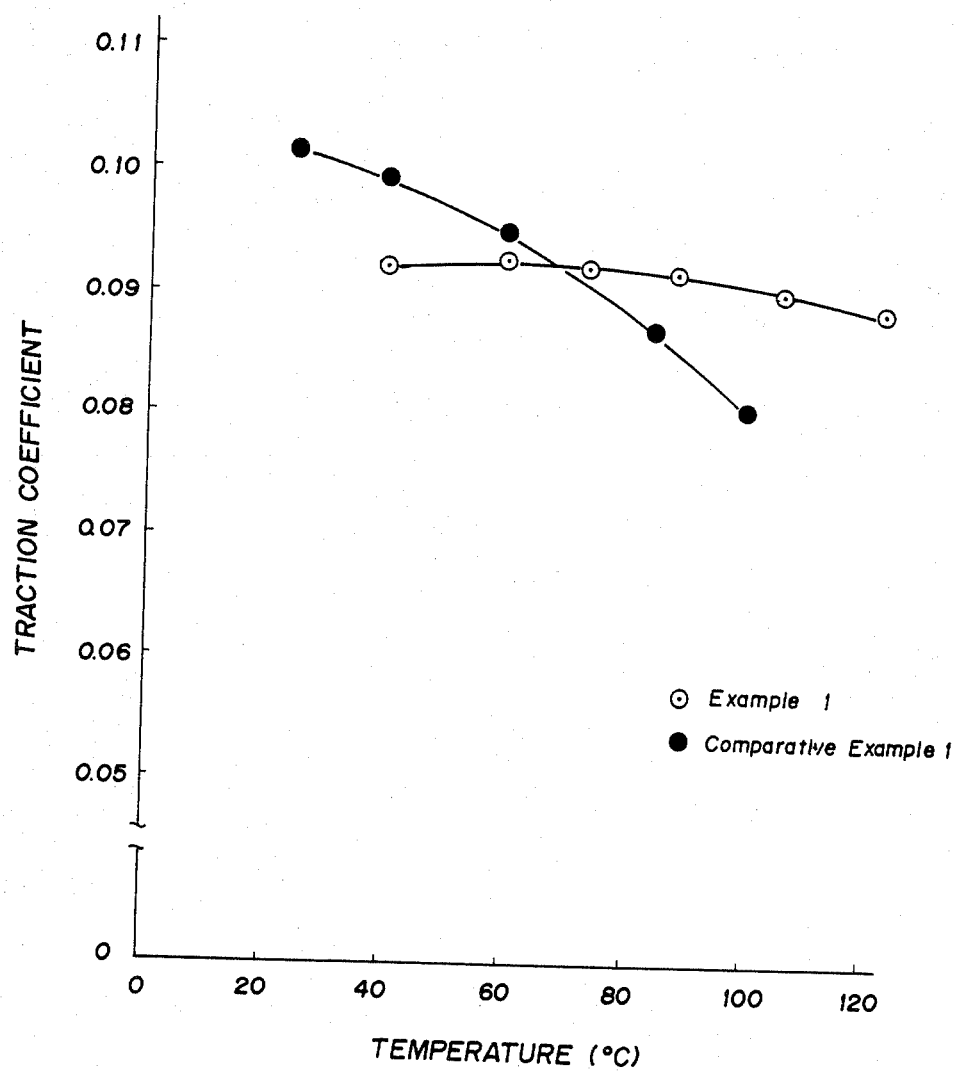
FIGS. 1, 2 and 3 are each a graph showing the temperature dependence of traction coefficient for the products obtained in the Examples and Comparative Examples.

Specific examples of the compounds represented by the general formula (I) are shown below:

1,1-Didecalylethane (I-1)

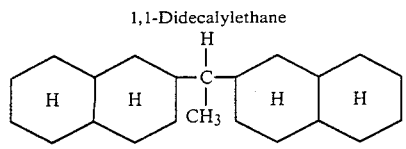

1,1-Didecalylpropane (I-2)

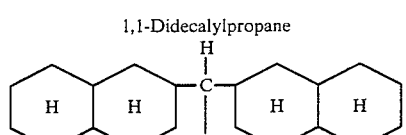

1,1-Didecalylbutane (I-3)

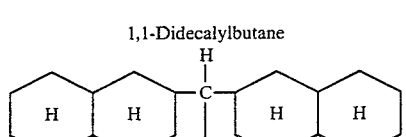

Specific examples of the compounds represented by the general formula (II) are shown below:

1,1-Di(bicyclohexyl)ethane (II-1)

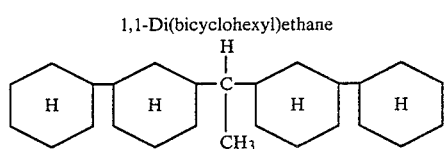

1,1-Di(bicyclohexyl)propane (II-2)

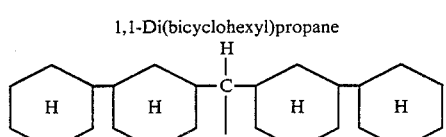

Specific examples of the compounds represented by the general formula (III) are shown below:

1-(2-Decalyl)-1-cyclohexylethane (III-1)

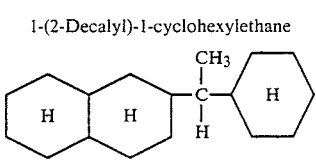

1-(1-Decalyl)-1-cyclohexylethane (III-2)

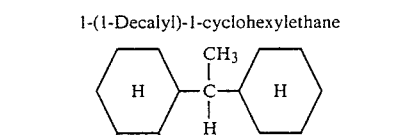

1-(2-Decalyl)-1-(4-(tert-butyl)cyclohexyl)ethane (III-3)

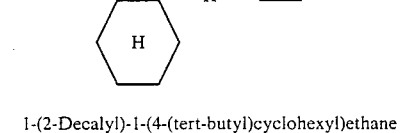

1-(1-Decalyl)-1-(4-(tert-butyl)cyclohexyl)ethane (III-4)

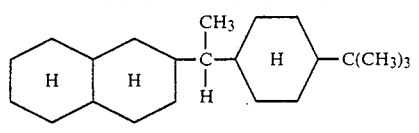

-continued

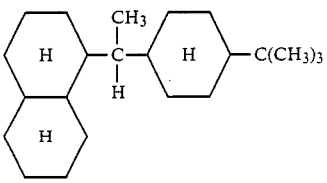

1-Dimethyldecalyl-1-cyclohexylethane (III-5)

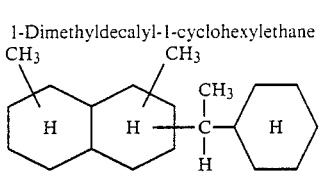

or

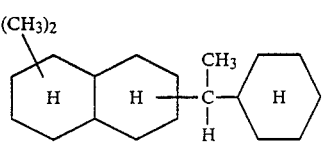

or

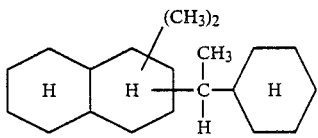

1-Methyldecalyl-1-cyclohexylethane (III-6)

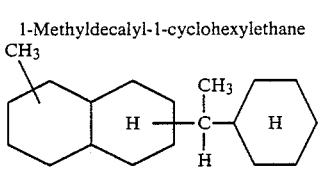

or

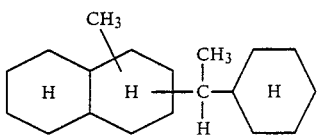

These compounds are used, alone or in combination with each other, as a base stock for a traction drive fluid.

The compounds represented by the general formulae (I), (II) and (III) can be prepared in any suitable manner. For example, 1,1-didecalylethane (Formula I-1) can be prepared by various techniques such as a method in which naphthalene and paraldehyde are reacted in the presence of a hydrogen fluoride catalyst and, thereafter, hydrogenated, and a method in which naphthalene and 1,1-dichloroethane are reacted in the presence of an aluminum chloride catalyst and, thereafter, hydrogenated.

Also, 1,1-di-(bicyclohexyl)ethane (Formula (II-1)) can be prepared by any suitable procedure, for example, the same methods as described above for the preparation of 1,1-didecalylethane can be employed with the exception that biphenyl is used in place of naphthalene.

As a typical method of preparation of the compounds of the general formula (III), there can be given a method in which tetralin or naphthalene, or its derivative, and styrene, or its derivative, is reacted in the presence of an acid catalyst, e.g., sulfuric acid, the thus-obtained reaction product is vacuum distilled into fractions, and a predetermined fraction is hydrogenated by the use of a catalyst. In the above methods, nickel, platinum, palladium, rhodium, ruthenium, etc. are preferable as the catalyst for hydrogenation, and especially platinum catalyst, rhodium catalyst and ruthenium catalyst are preferable since cis-form decalin ring is produced predominantly by the use of these catalysts. Traction coefficient of said cis-form compound is higher than that of trans-form compound.

The cis-form decalin ring herein means a decalin ring in which a hydrogen bonded to the carbon atom of 9-position and a hydrogen bonded to the carbon atom of 10-position are located in cis-position each other.

In general, 1-decalyl-1-cyclohexylethane and derivatives thereof represented by the general formula (III) are a mixture of the cis-form and the trans-form, and the trans-form is contained in a larger amount than that of the cis-form in the mixture.

In the present invention, however, the mixture in which the cis-form is contained in a larger amount is preferably used. From the standpoint of improving traction coefficient at high temperature, the mixture of more than 70% of the cis-form and less than 30% of the trans-form is preferable, and the mixture of more than 80% of the cis-form and less than 20% of the trans-form is most preferable.

An example of the compound represented by Formula (III-1) includes a mixture of more than 70% of 1-(2-cis-decalyl)-1-cyclohexylethane and less than 30% of 1-(2-trans-decalyl)-1-cyclohexylethane.

An example of the compound represented by Formula (III-2) includes a mixture of more than 70% of 1-(1-cis-decalyl)-1-cyclohexylethane and less than 30% of 1-(1-trans-decalyl)-1-cyclohexylethane.

The thus-prepared compound having the general formula (I), (II) or (III) can be used as such as a base stock for a traction drive fluid, and it has a superior traction coefficient which less changes over a wide temperature range (from room temperature to 140° C. (284° F.) and has a low viscosity. Since the compounds represented by the general formulae (I), (II) and (III) can be prepared relatively inexpensively by the above-described methods, the traction drive fluids used in the invention are inexpensive and advantageous from an economic viewpoint.

Since the traction drive fluid used in the invention, as described above, has a superior traction coefficient over from low temperatures to high temperatures, it contributes to the miniaturization of driving devices. Furthermore, the present traction drive fluid can be used under severe conditions of high-speed and high-load.

In accordance with the process of the present invention, traction coefficient of traction drive fluids in the traction driving device which is driven at high temperatures of 200° F. (93.3° C.) to 250° F. (121.1° C.) or more is remarkably improved. That is to say, traction drive fluids used in the present invention have higher traction coefficient at high temperatures than the conventional fluids, and are of high practical value. Therefore, the traction drive fluid of the invention can be widely used in various machines such as continuously variable transmission for cars or other industrial products and hydraulic machines.

The present invention is explained in greater detail by reference to the following Examples and Comparative Examples.

The traction coefficient was measured by the use of a two roller machine. One of two rollers, which were equal in size (diameter: 60 millimeters; thickness: 6 millimeters) and were in contact with each other along one line, was rotated at a predetermined rate (2,000 revolutions per minute (r.p.m.)), and the other was rotated at a predetermined lower rate (1,700 r.p.m.). A load of 140 kilograms was applied onto the contact line by means of a spring, and the torque was measured by means of a strain gauge and a torque meter. From the thus-measured value of torque, the traction coefficient was calculated. The two rollers were made of carbon steel, SCM--3, the surface of which was subjected to a buffing treatment using alumina (0.03 micron). The surface roughness was $R_{max}=0.2$ micron, and the Hertzian pressure in contact was 75 kilograms per square millimeter. This measurement was performed while changing the temperature of oil from room temperature to 120°-140° C. by heating an oil tank by means of a heater.

EXAMPLE 1

A mixture of 2,500 grams of tetralin and 500 grams of concentrated sulfuric acid was placed in a 5-liter glass flask, and the temperature in the flask was lowered to 0° C. by means of ice water. While vigorously stirring the mixture, 150 grams of paraldehyde was slowly dropped over 3 hours and, thereafter, the resulting mixture was further stirred for 1 hour to complete the reaction. At the end of the time, the stirring was stopped, and the reaction product was allowed to stand to separate an oil layer. The oil layer was then washed with 1 liter of a 2N aqueous solution of sodium hydroxide and 1 liter of saturated brine (NaCl), three times for each, and then dried over anhydrous sodium sulfate. Then, the unreacted tetralin was distilled away, and the residue was vacuum distilled to obtain 600 grams of a fraction having a boiling point of 165°-172° C./0.15 mmHg. Analysis showed that it was 1,1-ditetralylethane.

Five hundred milliliters of 1,1-ditetralylethane was placed in a 1-liter autoclave and, after addition of 50 grams of an activated nickel catalyst for hydrogenation (Catalyst N-112 produced by Nikki Kagaku Co., Ltd.), hydrogenated at a hydrogen pressure of 50 kilograms per square centimeter and a reaction temperature of 200° C. After cooling, the reaction solution was filtered to separate the catalyst. The light fraction was stripped and, thereafter, analyzed. It was confirmed that the degree of hydrogenation was over 99.9% (which was also confirmed by Nuclear Magnetic Reasonance (NMR) analysis), and that the compound was 1,1-didecalylethane. The refractive index, $n_D^{20}$, was 1.5176, the specific gravity was 0.97 (15/4° C.), and the dynamic viscosity was 12 centistokes (100° C.). The traction coefficient was measured over a temperature range of from 40° to 120° C. The results are shown in FIG. 1.

EXAMPLE 2

A mixture of 1,000 grams of tetralin and 300 grams of concentrated sulfuric acid was placed in a 3-liter glass flask, and the temperature in the flask was lowered to 0° C. on an ice bath. To the mixture was then slowly added dropwise 400 grams of styrene over 3 hours while stirring, and the resulting mixture was further stirred for 1 hour to complete the reaction. At the end of the time, stirring was stopped and the reaction mixture was allowed to stand to separate an oil layer. The oil layer was washed with 500 milliliters of a 1N aqueous solution of sodium hydroxide and 500 milliliters of saturated brine, three times for each, and then dried over anhydrous sodium sulfate. The unreacted tetralin was distilled away, and the residue was vacuum distilled to obtain 750 grams of a fraction having a boiling point of 135°–148° C./0.17 mmHg. Analysis showed that the fraction was a mixture of 1-(1-tetralyl)-1-phenylethane and 1-(2-tetralyl)-1-phenylethane.

Figure 2:
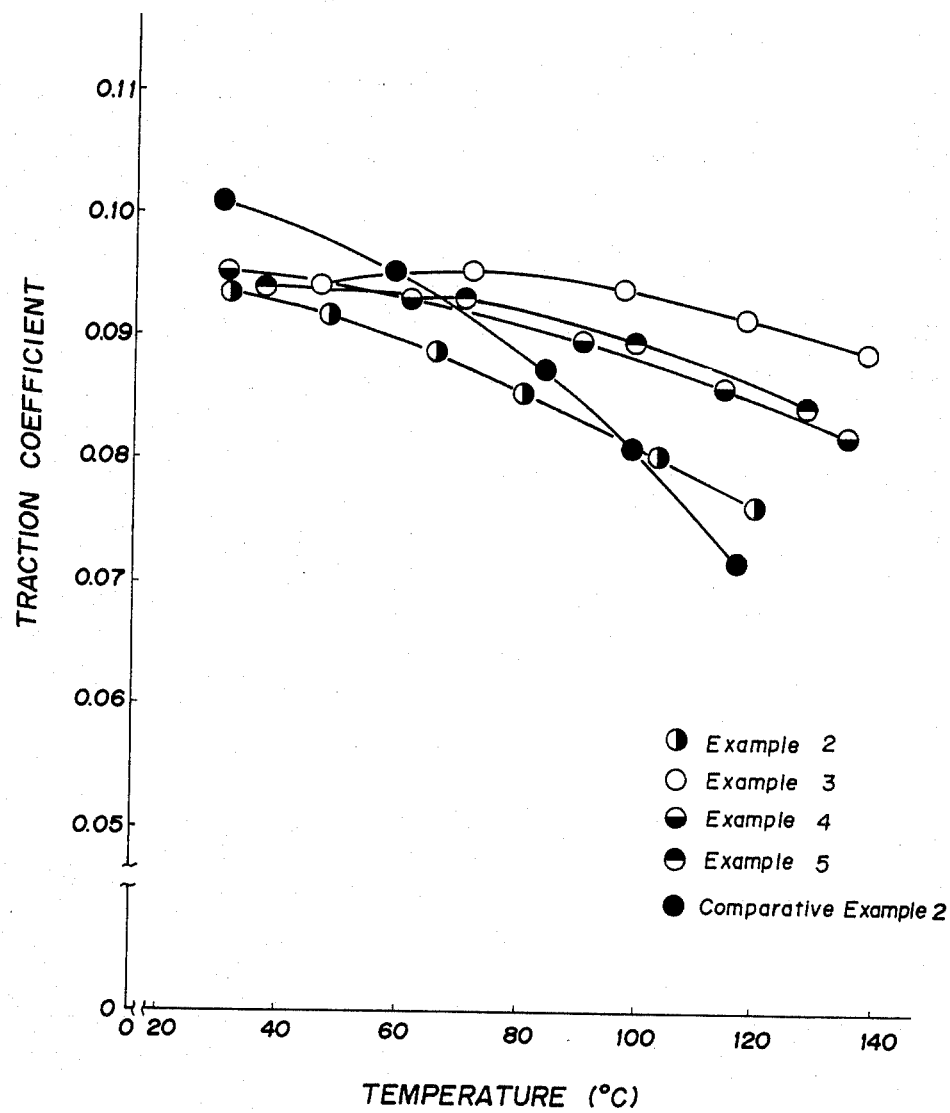

Five hundred milliliters of the above-obtained fraction was placed in a 1-liter autoclave and, after addition of 50 grams of an activated nickel catalyst for hydrogenation (trade name: Catalyst N-113, produced by Nikki Kagaku Co., Ltd.), hydrogenated at a hydrogen pressure of 50 kilograms per square centimeter and a reaction temperature of 200° C. for 4 hours. After cooling, the reaction solution was filtered to separate the catalyst. Subsequently, a light fraction was separated from the resulting filtrate by stripping, and analyzed. This analysis showed that the degree of hydrogenation was over 99.9%, and it was confirmed that the light fraction was a mixture of 1-(1-decalyl)-1-cyclohexylethane and 1-(2-decalyl)-1-cyclohexylethane. The specific gravity of the mixture was 0.94 (15/4° C.), the dynamic viscosity was 4.2 centistokes (100° C.), and the refractive index, $n_D^{20}$, was 1.5025. The cis-form content was 42% in the mixture. The traction coefficient was measured over a temperature range of from 30° to 120° C. The results are shown in FIG. 2.

EXAMPLE 3

In the same manner as in Example 2 except that 550 grams of p-(tert-butyl)styrene was used in place of styrene, 800 grams of a fraction having a boiling point of 180°–190° C./0.9 mmHg was obtained. Analysis showed that the fraction was a mixture of 1-(1-tetralyl)-1-(p-(tert-butyl)phenyl)ethane and 1-(2-tetralyl)-1-(p-(tert-butyl)phenyl)ethane.

The fraction was then subjected to a hydrogenation treatment and stripping in the same manner as in Example 2. The thus-obtained product was a mixture of 1-(1-decalyl)-1-(4-(tert-butyl)cyclohexyl)ethane and 1-(2-decalyl)-1-(4-(tert-butyl)cyclohexyl)ethane. The specific gravity of the mixture was 0.92 (15/4° C.), the dynamic viscosity was 10 centistokes (100° C.), and the refractive index, $n_D^{20}$, was 1.4998. The traction coefficient of the product was measured over a temperature range of from 40° to 140° C. The results are shown in FIG. 2.

EXAMPLE 4

In accordance with the same process as in Example 2 except that 1,000 grams of dimethylnaphthalene (a dimethylnaphthalene mixture produced by Wako Junyaku Co., Ltd.) was used in place of tetralin, a mixture of 1-(1-dimethyldecalyl)-1-cyclohexylethane and 1-(2-dimethyldecalyl)-1-cyclohexylethane was produced. The specific gravity of the mixture was 0.93 (15/4° C.), the dynamic viscosity was 5.6 centistokes (100° C.), and the refractive index, $n_D^{20}$, was 1.5007. The traction coefficient of the product was measured over a temperature range of from 40° to 140° C. The results are shown in FIG. 2.

EXAMPLE 5

In accordance with the same process as in Example 2 except that a mixture of 500 grams of α-methylnaphthalene and 500 grams of β-methylnaphthalene was used in place of tetralin, a mixture of 1-(1-methyldecalyl)-1-cyclohexylethane and 1-(2-methyldecalyl)-1-cyclohexylethane was produced. The specific gravity of the mixture was 0.94 (15/4° C.), the dynamic viscosity was 5.8 centistokes (100° C.), and the refractive index, $n_D^{20}$, was 1.5069. The traction coefficient of the product was measured over a temperature range of from 40° to 130° C. The results are shown in FIG. 2.

COMPARATIVE EXAMPLE 1

A mixture of 1,000 grams of α-methylstyrene, 50 grams of acidic terra abla, and 50 grams of ethylene glycol was placed in a 3-liter glass flask, and reacted with stirring at 140° C. for 2 hours. The catalyst was removed from the reaction solution by filteration. Then, the unreacted α-methylstyrene and ethylene glycol were distilled away to obtain 900 grams of a fraction having a boiling point of 125°–130° C./0.2 mmHg. NMR analysis and gas chromatographic analysis confirmed that the fraction was a mixture consisting of 95% α-methylstyrene linear dimer and 5% α-methylstyrene cyclic dimer.

The fraction was subjected to hydrogenation and post-treatment in the same manner as in Example 1 to obtain a traction drive fluid composed mainly of 2,4-bicyclohexyl-2-methylpentane. The refractive index, $n_D^{20}$, of the thus-formed fluid was 1.4902, the specific gravity was 0.90 (15/4° C.), the dynamic viscosity was 3.7 centistokes (100° C.), and the viscosity index was 16. The traction coefficient was measured over a temperature range of from 25° C. to 100° C. The results are shown in FIG. 1.

It can be seen from FIG. 1 that the traction coefficient of the fluid at high temperatures is low compared with that of the fluid of the present invention.

COMPARATIVE EXAMPLE 2

The traction coefficient of the traction drive fluid produced in Comparative Example 1 was measured over a temperature range of from 30° to 120° C. The results are shown in FIG. 2.

EXAMPLE 6

Figure 3:
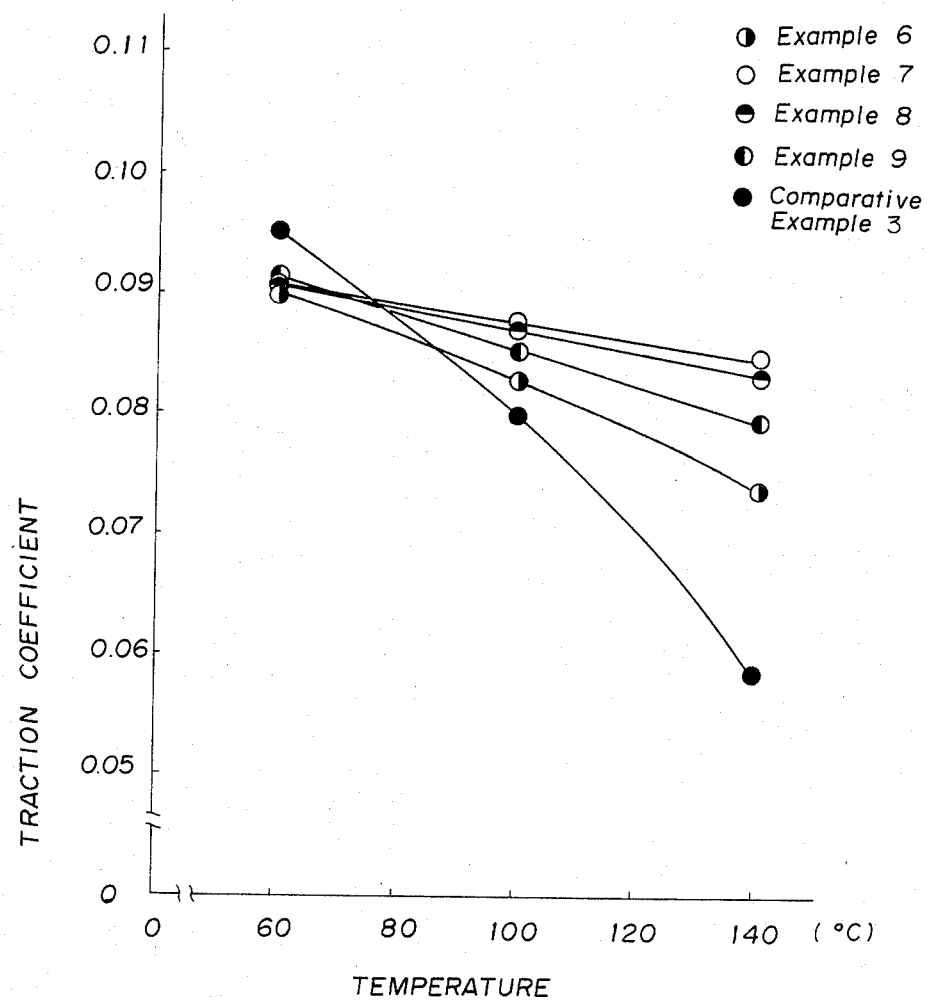

In accordance with the same process as in Example 2 except that 50 grams of 0.5% platinum-alumina catalyst (produced by Nippon Engelhard Co., Ltd.) was used in place of the activated nickel catalyst, a mixture of 1-(1-decalyl)-1-cyclohexylethane and 1-(2-decalyl)-1-cyclohexylethane was produced. In the mixture, the cis-form, that is 1-(1-cis-decalyl)-1-cyclohexylethane and 1-(2-cis-decalyl)-1-cyclohexylethane, was contained in the ratio of 71%. The specific gravity of the mixture was 0.94 (15/4° C.), the dynamic viscosities were 34 centistokes (40° C.) and 4.6 centistokes (100° C.), and the refractive index, $n_D^{20}$, was 1.5040. The traction coefficient was measured over a temperature range of from 60° to 140° C. The results are shown in FIG. 3.

EXAMPLE 7

In accordance with the same process as in Example 2 except that (i) 20 grams of 5% ruthenium-carbon catalyst (produced by Nippon Engelhard Co., Ltd.) was used in place of the activated nickel catalyst, (ii) a hydrogen pressure was 20 kilograms per square centimeter, and (iii) a reaction temperature for hydrogenation was 120° C., a mixture of 1-(1-decalyl)-1-cyclohexylethane and 1-(2-decalyl)-1-cyclohexylethane was produced. The cis-form content was 88% in the mixture.

The specific gravity of the mixture was 0.94 (15/4° C.), the dynamic viscosities were 39 centistokes (40° C.) and 4.9 centistokes (100° C.), and the refractive index, $n_D^{20}$, was 1.5048. The traction coefficient was measured over a temperature range of from 60° to 140° C. The results are shown in FIG. 3.

EXAMPLE 8

In accordance with the same process as in Example 2 except that (i) 15 grams of 5% rhodium-carbon catalyst (produced by Nippon Engelhard Co., Ltd.) was used in place of the activated nickel catalyst and (ii) a reaction temperature for hydrogenation was 80° C., a mixture of 1-(1-decalyl)-1-cyclohexylethane and 1-(2-decalyl)-1-cyclohexylethane was produced. The cis-form content as 86% in the mixture. The specific gravity of the mixture was 0.94 (15/4° C.), the dynamic viscosities were 37 centistokes (40° C.) and 4.7 centistokes (100° C.), and the refractive index, $n_D^{20}$, was 1.5047. The traction coefficient was measured over a temperature range of from 60° to 140° C. The results are shown in FIG. 3.

EXAMPLE 9

In accordance with the same process as in Example 2 except that 1,000 grams of naphthalene and 3,000 milliliters of carbon tetrachloride were used in place of 1,000 grams of tetralin, a mixture of 1-(1-naphthyl)-1-phenylethane and 1-(2-naphthyl)-1-phenylethane was produced.

The mixture produced was hydrogenated in the same manner as in Example 2 except that (i) 10 grams of 5% ruthenium-carbon catalyst (same as in Example 7) and 10 grams of water were used in place of the activated nickel catalyst, (ii) a hydrogen pressure was 70 kilograms per square centimeter, and (iii) a reaction temperature for hydrogenation was 150° C., a mixture of 1-(1-decalyl)-1-cyclohexylethane and 1-(2-decalyl)-1-cyclohexylethane was produced. The cis-form content was 83% in the mixture. The specific gravity of the mixture was 0.94 (15/4° C.), the dynamic viscosities were 38 centistokes (40° C.) and 4.9 centistokes (100° C.), and the refractive index, $n_D^{20}$, was 1.5050. The traction coefficient was measured over a temperature range of from 60° to 140° C. The results are shown in FIG. 3.

COMPARATIVE EXAMPLE 3

The traction coefficient of the traction drive fluid produced in Comparative Example 1 was measured over a temperature range of from 60° to 140° C. The results are shown in FIG. 3.

What is claimed is:

1. A process for improving the coefficient of traction between at least two relatively rotatable elements in a torque transmitting relationship and for maintaining said coefficient of traction substantially constant over a broad range of operating temperatures which comprises introducing between the tractive surfaces of said elements a traction drive fluid comprising at least one compound represented by the general formulae (I), (II) and (III):

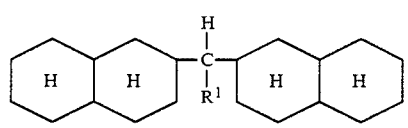

(I)

wherein $R^1$ is an alkyl group containing from 1 to 3 carbon atoms,

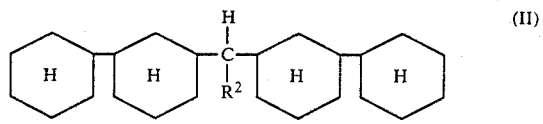

(II)

wherein $R^2$ is an alkyl group containing 1 or 2 carbon atoms,

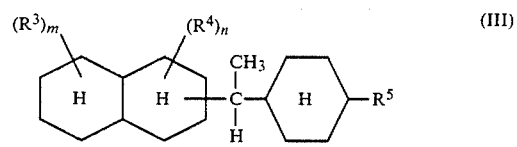

(III)

wherein $R^3$ and $R^4$ are each a hydrogen or a methyl group, $R^5$ is a hydrogen or a tert-butyl group, and m and n are each 1 or 2, said compound (III) comprising a mixture of more than 70% of the cis form and less than 30% of the trans form.

2. The process of claim 1, wherein the compound represented by the general formula (I) is 1,1-didecalylethane of the formula:

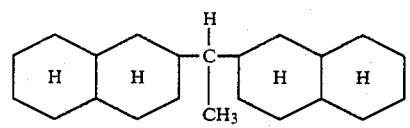

3. The process of claim 1, wherein the compound represented by the general formula (I) is 1,1-didecalylpropane of the formula:

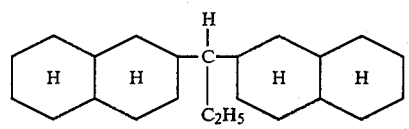

4. The process of claim 1, wherein the compound represented by the general formula (I) is 1,1-didecalylbutane of the formula:

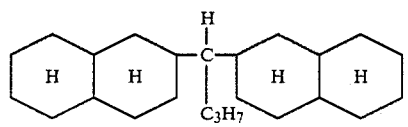

5. The process of claim 1, wherein the compound represented by the general formula (II) is 1,1-di(bicyclohexyl) ethane of the formula:

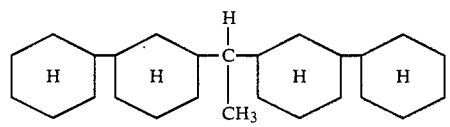

6. The process of claim 1, wherein the compound represented by the general formula (II) is 1,1-di-(bicyclohexyl) propane of the formula:

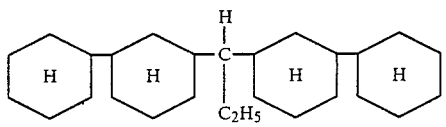

7. The process of claim 1, wherein the compound represented by the general formula (III) is 1-(2-decalyl)-1-cyclohexylethane of the formula:

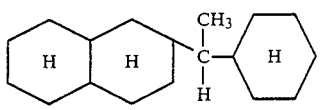

8. The process of claim 1, wherein the compound represented by the general formula (III) is 1-(1-decalyl)-1-cyclohexylethane of the formula:

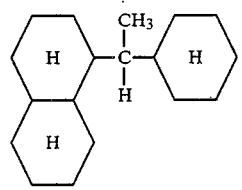

9. The process of claim 1, wherein the compound represented by the general formula (III) is 1-(2-decalyl)-1-(4-tert-butyl)cyclohexyl)-ethane of the formula:

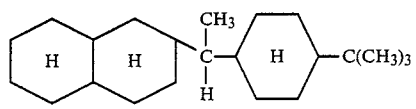

10. The process of claim 1, wherein the compound represented by the general formula (III) is 1-(1-decalyl)-1-(4-(tert-butyl)cyclohexyl)-ethane of the formula:

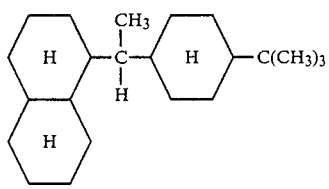

11. The process of claim 1, wherein the compound represented by the general formula (III) is 1-dimethyl-decalyl-1-cyclohexylethane of the formula:

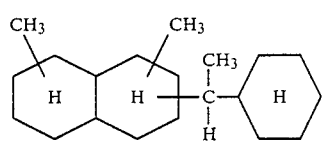

or

-continued

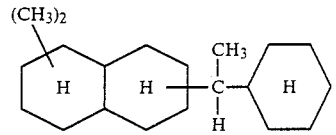

or

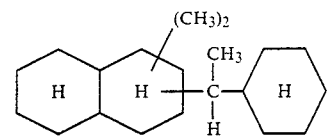

12. The process of claim 1, wherein the compound represented by the general formula (III) is 1-methyl-decalyl-1-cyclohexylethane of the formula:

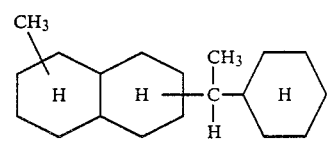

or

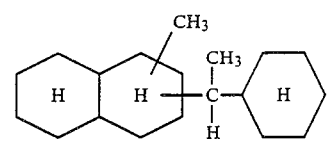

13. A traction drive fluid composition for use between at least two relatively rotatable elements in a torque transmitting relationship which comprises as the principal component at least one compound represented by the general formulae (I), (II) and (III):

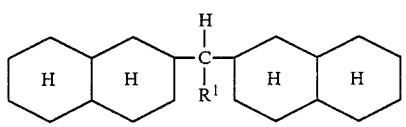

wherein $R^1$ is an alkyl group containing from 1 to 3 carbon atoms,

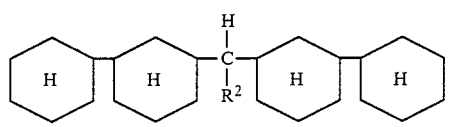

wherein $R^2$ is an alkyl group containing 1 or 2 carbon atoms,

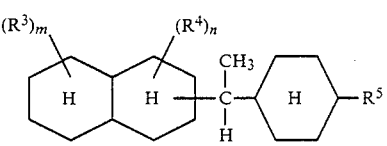

wherein $R^3$ and $R^4$ are each a hydrogen or a methyl group, $R^5$ is a hydrogen or a tert-butyl group, and m and n are each 1 or 2, said compound (III) comprising a mixture of more than 70% of the cis form and less than 30% of the trans form.

14. A traction drive fluid composition according to claim 13 wherein the compound represented by the general formula (I) is 1,1-didecalylethane.

15. A traction drive fluid composition according to claim 13 wherein the compound represented by the general formula (I) is 1,1-didecalylpropane.

16. A traction drive fluid composition according to claim 13 wherein the compound represented by the general formula (I) is 1,1-didecalylbutane.

17. A traction drive fluid composition according to claim 13 wherein the compound represented by the general formula (II) is 1,1-di(bicyclohexyl)ethane.

18. A traction drive fluid composition according to claim 13 wherein the compound represented by the general formula (II) is 1,1-di-(bicyclohexyl)propane.

19. A traction drive fluid composition according to claim 13 wherein the compound represented by the general formula (III) is 1-(2-decalyl)-1-cyclohexylethane.

20. A traction drive fluid composition according to claim 13 wherein the compound represented by the general formula (III) is 1-(1-decalyl)-1-cyclohexylethane.

21. A traction drive fluid composition according to claim 13 wherein the compound represented by the general formula (III) is 1-(2-decalyl)-1-(4-(tert-butyl)cyclohexyl)ethane.

22. A traction drive fluid composition according to claim 13 wherein the compound represented by the general formula (III) is 1-(1-decalyl)-1-(4-(tert-butyl)cyclohexyl)ethane.

23. A traction drive fluid composition according to claim 13 wherein the compound represented by the general formula (III) is 1-dimethyldecalyl-1-cyclohexylethane of the formula:

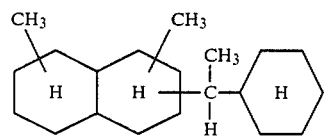

or

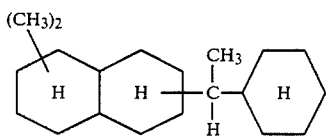

or

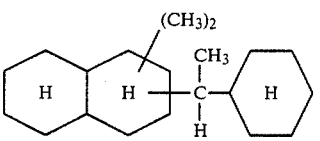

24. A traction drive fluid composition according to claim 13 wherein the compound represented by the general formula (III) is 1-methyldecalyl-1-cyclohexylethane of the formula:

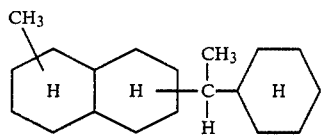

or

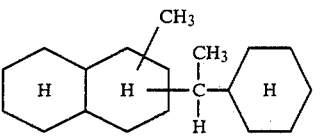

* * * * *